United States Patent [19]
Tu et al.

[11] Patent Number: 6,113,593
[45] Date of Patent: Sep. 5, 2000

[54] ABLATION APPARATUS HAVING TEMPERATURE AND FORCE SENSING CAPABILITIES

[76] Inventors: Lily Chen Tu; Hosheng Tu, both of 2151 Palermo, Tustin, Calif. 92782

[21] Appl. No.: 09/241,972

[22] Filed: Feb. 1, 1999

[51] Int. Cl.[7] .................................................. A61B 18/12
[52] U.S. Cl. .............................. 606/34; 606/38; 606/41; 600/374; 607/99; 607/105; 607/113
[58] Field of Search ................................. 606/34, 38, 41, 606/49; 607/99, 105, 113, 122; 600/587, 374

[56] References Cited

U.S. PATENT DOCUMENTS

| | | | |
|---|---|---|---|
| 5,255,679 | 10/1993 | Imran | 128/642 |
| 5,396,887 | 3/1995 | Imran | 128/642 |
| 5,529,067 | 6/1996 | Larsen et al. | 128/642 |
| 5,658,278 | 8/1997 | Imran et al. | 606/41 |
| 5,893,848 | 4/1999 | Negus et al. | 606/41 |
| 5,913,856 | 6/1999 | Chia et al. | 606/41 |
| 6,039,731 | 3/2000 | Taylor et al. | 606/41 |

*Primary Examiner*—Lee Cohen

[57] ABSTRACT

An ablation apparatus system for treating tissues in a patient, the ablation apparatus comprising temperature sensing means for measuring a temperature, wherein said temperature sensing means comprises a temperature sensing probe and at least one temperature sensing wire secured to the temperature sensing probe; force measuring means for measuring force exerted onto the temperature sensing probe by a tissue; and RF current generating means for generating RF current, wherein the RF current generating means is connected to and controlled by the temperature sensing means and force measuring means, adapted for supplying RF current to the temperature sensing probe as an electrode for tissue treatment.

14 Claims, 4 Drawing Sheets

ABLATION APPARATUS HAVING TEMPERATURE AND FORCE SENSING CAPABILITIES

The present invention generally relates to improved medical apparatus and methods for treating tissues, and more particularly, to such an ablation apparatus and methods for treating brain, nerve, capillary, or liver tissues in a patient by delivering controlled therapeutic RF energy through a temperature sensing probe for treating the specific tissue, wherein RF energy delivery is controlled by temperature sensing means and force measuring means.

BACKGROUND OF THE INVENTION

A capillary is one of the tube-shaped blood vessels that carry blood away from the arterioles to the body's tissues and organs. When a capillary is impaired, radiofrequency (RF) therapy can be applied to the capillary to treat the tissue. To ensure appropriate treatment, temperature at the lesion is sensed and the temperature reading is transmitted to an external monitor for temperature monitoring and for controlling RF energy delivery. It is also important that the force at the catheter tip is within reasonably acceptable range so that not to injure the tissue. A typical ablation device includes an electrode for RF energy delivery and a temperature sensor for measuring tissue temperature. The bulky size of said ablation device comprising an electrode and a temperature probe might pose safety concerns to a patient when it is forced into a restricted place. A miniature RF-delivery apparatus is needed to pass into tiny openings for capillary treatment, the apparatus preferably having temperature sensing means for sensing/controlling the RF energy delivery and force measuring means for sensing/controlling apparatus advancement.

A liver cancer or tumor is difficult to treat because of its softness. RF therapy has been applied to treat the liver tissue. It is also important that the force at the catheter tip is within reasonably acceptable range for contacting the liver tissue so that not to injure the liver tissues. However, the existing ablation device can only treat the surface of the liver because of its bulky construction comprising at least one electrode and a temperature sensor. A miniature RF-delivery apparatus is needed to reach a liver and optionally into the liver for therapeutic treatment, the apparatus preferably having temperature sensing means for sensing/controlling the RF energy delivery and force measuring means for sensing/controlling apparatus advancement.

Similarly, a nerve is located within a restricted space which is difficult for a bulky ablation device to access to. A miniature RF-delivery apparatus is needed to reach a nerve for therapeutic treatment, the apparatus preferably having temperature sensing means and force measuring means. In all the above indications, a miniature RF-delivery apparatus should have temperature sensing means for controlling the RF energy delivery according to the appropriate temperature prescribed; and force measuring means for controlling RF energy delivery and for apparatus advancement operations according to the appropriate force prescribed.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective.

RF therapeutic protocol has been proven to be highly effective when used by electrophysiologists for the treatment of tachycardia; by urologists for treatment of prostates; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. RF energy, when coupled with a temperature control mechanism, can be supplied precisely to the apparatus-to-tissues contact site to obtain the desired temperature for treating a tissue.

A thermocouple is a temperature sensing probe consisting of the junction of two dissimilar metals which has a millivolt output proportional to the difference in temperature between the "hot" junction and the lead wires (cold junction). Temperature sensing using a thermocouple is based on the discovery by Seebeck in 1821 that an electric current flows in a continuous circuit of two different metallic wires if the two junctions are at different temperatures. In electric circuits, the current is dependent on the electromotive force developed and the resistance of the circuit. For accurate temperature measurements, the measuring instrument is constructed so that a no-current electromotive force is measured to eliminate the effects of circuit resistance. The materials used for the wires typically include copper, nickel-chromium, iron, platinum, nickel-aluminum, and Constantan. A good reference book for more information on thermocouples is Perry's Chemical Engineer's Handbook $6^{th}$ Edition, published by McGraw-Hill Book Company, 1973.

A thermistor is a temperature-sensing probe manufactured of a mixture of metal oxides. A large change in resistance is exhibited proportional to a change in temperature. Electrical conductors experience a change in resistance with temperature which can be measured with a Wheat-stone-bridge circuit. The relationship for platinum is very exact and hence serves as a primary standard over a wide temperature range. A good reference book for more information on thermistors is Mark's Standard Handbook for Mechanical Engineers $8^{th}$ Edition, published by McGraw-Hill Book Company, 1978.

Thermostatic bimetal thermometers can be defined as a composite material made up of strips of two or more metals fastened together. Types of elements used in bimetal thermometers are flat spiral, single helix, and multiple helix. This composite, because of the different expansion rates of its components, tends to change curvature when subjected to a change in temperature. The distal portion of a bimetal thermometer can be straightened to function as an electrode for RF energy delivery to a tissue.

One major drawback of the current RF ablation devices is its bulkiness. In addition to its bulkiness, the force for pushing a conventional catheter into a confined space is not monitored and controlled. A patient is in great risk of injury when the force is undesirably higher than an accepted value. A force measuring means on a RF catheter would request a physician to take appropriate actions when he receives a warning. An existing RF ablation catheter generally comprises at least one electrode and its associated temperature sensing probes. The total space needed for an electrode and its additional temperature probe makes said device not suitable for certain tissue ablation applications due to its restricted location or space. Therefore, there is a clinical need for an improved ablation apparatus system having capabilities of measuring a contact force, measuring a tissue temperature, delivering RF therapeutic energy, and/or controlling the energy delivered for optimal effectiveness in tissue treatment.

SUMMARY OF THE [ ]INVENTION

In general, it is an object of the present invention to provide a method and an improved ablation apparatus system for generating heat to treat the nerve, brain, capillary, liver, or other tissues. It is another object of the present invention to provide a method and an apparatus system for monitoring the temperature of the ablated tissue and to control the tissue temperature by utilizing a temperature control mechanism and/or algorithm for energy delivery. It is still another object of this invention to provide a method and an ablation apparatus system for treating nerve, brain, capillary, liver, or other tissues in a patient by applying RF current through a temperature sensing wire to a temperature sensing probe, wherein the temperature sensing probe has duel functions of temperature sensing as a probe and energy delivery as an electrode. It is a further object of the present invention to provide an ablation apparatus for measuring force exerted by a contact tissue to the temperature sensing probe or to an electrode of a catheter.

Briefly, heat is generated by supplying a suitable energy source to an apparatus, which is comprised of at least one electrode means, in contact with the body tissues. The "electrode means" in this invention may either comprise a temperature sensing probe of the temperature sensing means for sensing the tissue temperature or a standard electrode having a conducting wire. A suitable energy source may consist of radiofrequency energy, microwave energy, ultrasonic energy, alternating current energy, or laser energy. The energy can be applied to the temperature sensing probe and consequently to the tissues through the electrode means of this invention. A DIP (dispersive indifferent pad) pad or electrode, that contacts the patient, is connected to the Indifferent Electrode Connector on the RF generator. Therefore, the RF energy delivery becomes effective when a close circuit from a RF generator through a patient and returning to the RF generator is formed. The generator should be grounded to avoid electrical interference. Heat is controlled by the power of the RF energy delivered, the delivery mode, and by the delivery duration. The RF energy may be delivered in a continuous mode, in a pulsed mode, or random mode as needed. The standard RF energy generator means and its applications through electrode means, to a patient are well known for those who are skilled in the art.

Force nay be measured by the deflection of an elastic element, by balancing against a known force, by the acceleration produced in an object of known mass, or by its effects on the electrical or other properties of a stress-sensitive material. The common unit of force is the "pound" (Newton). Since weight is the force of gravity acting on a mass, any of the weight-measuring devices can be used to measure force. Common methods employ the deflection of spring or cantilever beams. Elastic-element measuring devices are those in which the measured force deforms some elastic material within its elastic limit, the magnitude of the deformation being approximately proportional to the applied force.

A strain gauge is an element whose electrical resistance changes with applied strain. Measure of the resistance change can be translated into a measure of the force applied. The piezoelectric effect is useful in measuring rapidly varying forces because of its high-frequency response and negligible displacement characteristics. Quartz, rochelle salts, and barium titanate are common piezoelectric materials, They have the property of varying an output charge in direct proportion to the stress applied. This produces a voltage inversely proportional to the circuit capacitance. This is called a piezoelectric transducer or a piezoresistive transducer.

Strain measurements down to one-millionth inch per inch are possible with electrical-resistance wire gages. The signal is read or recorded by a galvanometer, oscilloscope, or other device. Equipment specifically constructed for strain measurement is available to indicate, record or transmit the signal for process control purposes.

In a preferred embodiment, an ablation apparatus system comprises (a) temperature sensing means for measuring a temperature, wherein said temperature sensing means comprises a temperature sensing probe and at least one temperature sensing wire secured to the temperature sensing probe, the temperature sensing probe being adapted for tissue contact; (b) force measuring means for measuring force exerted onto the temperature sensing probe by a contacted tissue; and (c) RF current generating means for generating RF current, wherein the RF current generating means is connected to the at least one temperature sensing wire of the temperature sensing means, the RF current generating means being adapted for delivering RF current to the temperature sensing probe. In an alternate embodiment, the RF current generating means is further connected to the force measuring means. The force sensed by the force measuring means of the apparatus is either used for controlling the RF current delivery to a tissue or used to adjust the operational procedures.

The ablation apparatus system further comprises temperature control means for receiving temperature readings, wherein the temperature reading measured from the temperature sensing means is relayed to the temperature control means and is adapted to effect the RF current delivery to the temperature sensing probe of the ablation apparatus system. The RF current is preferably within the range of 50 to 2,000 kHz.

In one preferred embodiment, the ablation apparatus system further comprises force control means for receiving force readings, wherein the force reading measured from the force measuring means is relayed to the force control means and is adapted to effect the RF current delivery to the temperature sensing probe or an electrode of the ablation apparatus system. In another preferred embodiment, the at least one temperature sensing wire is preferably a rigid wire for transmitting force measured by the force measuring probe or a temperature probe as force measuring means. The force measuring means is selected from a group consisting of a strain gauge, a spring instrument, a cantilever instrument, a piezoelectric transducer, an elastic-element measuring device, a piezoresistive transducer, and the like. A force measuring means is well known to one who is skilled in the art.

The temperature sensing means may consist of a thermocouples type temperature probe, a thermistor type temperature probe, a bimetal thermometers type temperature probe, and the like. In a further embodiment, the temperature sensing means is enclosed within an elongate tubular shaft for protection or strength supporting, wherein the elongate tubular shaft may further comprise a fluid passageway adapted for receiving fluid from a fluid source and venting fluid out of the elongate tubular shaft. In another embodiment, a distal portion of the elongate tubular shaft is conductive and is in contact with a portion of the temperature sensing probe or the at least one temperature sensing wires.

In an alternate embodiment, an ablation apparatus system comprises (a) a catheter shaft having a distal section, a distal end, a proximal end and a lumen extending between the distal end and the proximal end, wherein at least one electrode is mounted on the distal section; (b) force measuring means for measuring force exerted onto the distal end by a contact tissue; and (c) RF current generating means for generating RF current, wherein the RF current generating means is connected to the at least one electrode and to the force measuring means, the RF current generating means being adapted for delivering RF current to the at least one electrode. The ablation apparatus system further comprises force control means for receiving force readings, wherein the force measured from the force sensing means is relayed to the force control means and is adapted to effect the RF current delivery to the at least one electrode of the ablation apparatus system. The at least one electrode may be selected from a group consisting of a loop electrode, a cap electrode, a coil electrode, a mesh electrode, and a split-tip electrode.

A method for treating a tissue of a patient, the method comprises the steps of (a) inserting an ablation apparatus through an opening to a location of the tissue to be treated, the ablation apparatus system comprising temperature sensing means for measuring a temperature, wherein said temperature sensing means comprises a temperature sensing probe and at least one temperature sensing wire secured to the temperature sensing probe, the temperature sensing probe being adapted for tissue contact; force measuring means for measuring force exerted onto the temperature sensing probe by a contacted tissue; and RF current generating means for generating RF current, wherein the RF current generating means is connected to the at least one temperature sensing wire of the temperature sensing means and to the force measuring means, the RF current generating means being adapted for delivering RF current to the temperature sensing probe; (b) positioning the temperature sensing probe at the tissue to be treated; and (c) applying RF current through the temperature sensing wire to the temperature sensing probe to effect treatment of the tissue.

The method for treating a tissue may further comprise temperature control means for receiving temperature readings, the method further comprising relaying measured temperature from the temperature sensing means to the temperature control means, adapted to effect the RF current delivery to the temperature sensing probe of the ablation apparatus system. Alternately, the method for treating a tissue may further comprise force control means for receiving force readings and relaying measured force to the force control means, adapted to effect the RF current delivery to the electrode of the ablation apparatus system. The tissue for treatment is selected from a group consisting of a liver tissue, a tumor, a cancer, a prostate, a canker, a capillary, a brain tissue, and a nerve tissue.

The method and medical apparatus of the present invention has several significant advantages over other known systems or techniques to treat the tissues located close to a restricted location or space. In particular, the ablation apparatus system comprising the temperature sensing means, force measuring means, and RF energy delivery means using the temperature sensing probe as an electrode results in a more efficient therapeutic effect to the difficult-to-access tissues.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 4, what is shown is an embodiment of the ablation apparatus system, comprising three main components: temperature sensing means for measuring tissue temperature, force measuring means for sensing a force exerted by a contact, and RF generating means for delivering RF energy to a temperature sensing probe of the temperature sensing means.

Figure 1:
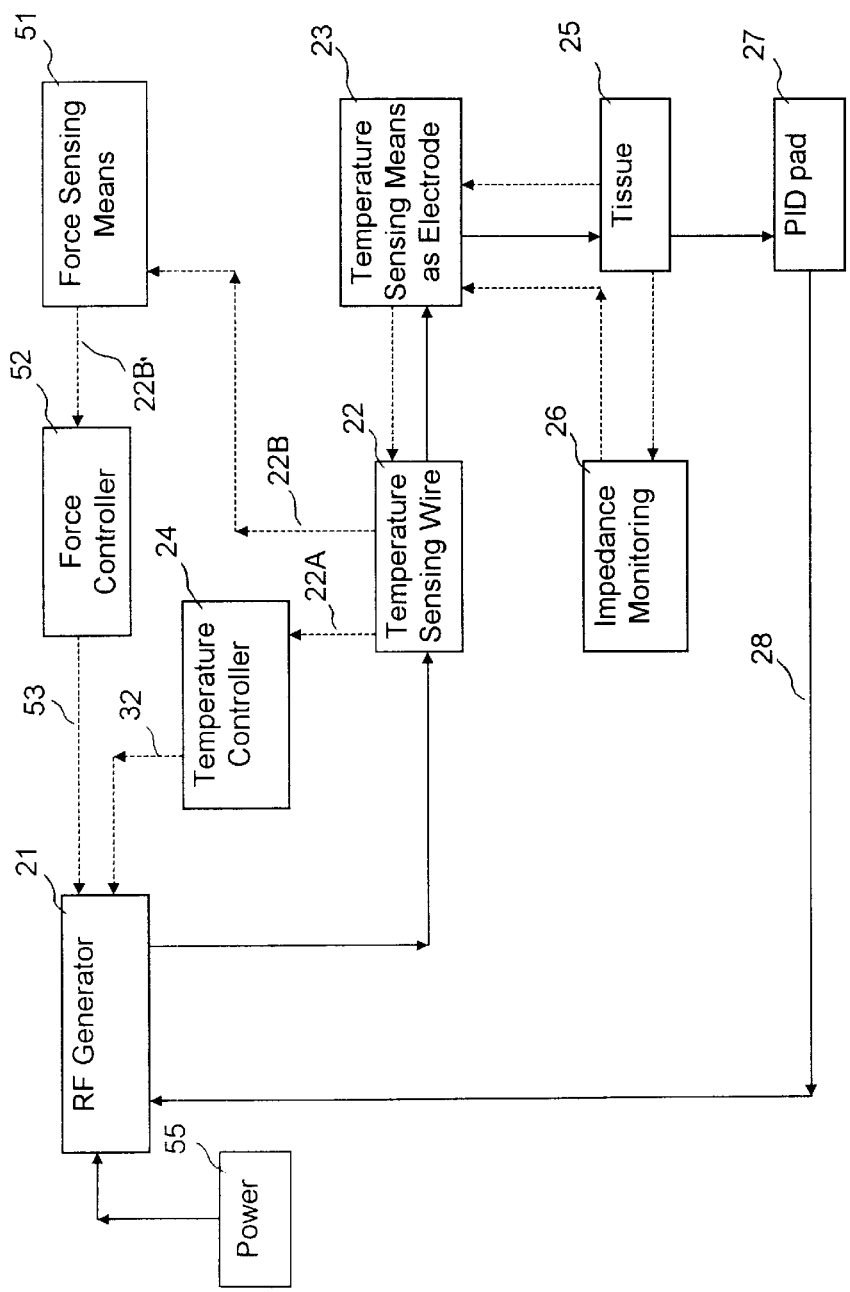
FIG. 1 is a schematic diagram of a RF treatment method in relation to the tissues through a temperature sensing probe as an electrode in a patient.

FIG. 1 shows a schematic diagram of a RF treatment method in relation to the tissues through a temperature sensing probe as an electrode in a patient. A RF generator 21 is connected to a temperature sensing probe 23 through a temperature sensing wire 22. The temperature sensing probe 23 is in close contact with the underlying tissue 25. A DIP (dispersive indifferent pad) type pad 27, that contacts the patient, is connected through a connecting cable 28 to the Indifferent Electrode Connector on the RF generator 21. Therefore, the RF energy delivery becomes effective when a close circuit from a RF generator through a patient and returning to the RF generator is formed.

Impedance 26 measured from the tissue contact 25 is to ensure good tissue contact for ablation, otherwise the RF power is cutoff when the impedance is unreasonably high. A temperature sensing probe 23 is also used to measure the tissue temperature and is relayed through a temperature sensing wire 22 and 22A to a closed-loop temperature controller 24 for controlling the ablative energy delivered through a transmitting medium 32. A force sensing means 51 may employ the temperature sensing probe 23 or an optional tip electrode to sense the force exerted by a tissue 25 on the catheter tip. The force is transmitted through a rigid portion of the temperature sensing wires 22 to the force sensing means 51. The measured force from the force measuring means 51 is relayed through another wire 22B to a force controller 52, whereas the signals from the force control means 52 may be used to effect the RF delivery or to adjust the operational procedures. Heat is controlled by the power of the RF energy delivered and by the delivery duration. The impedance monitoring route, the force monitoring route, and the temperature monitoring route as shown in FIG. 1 are used to assist the RF operation.

Figure 2:
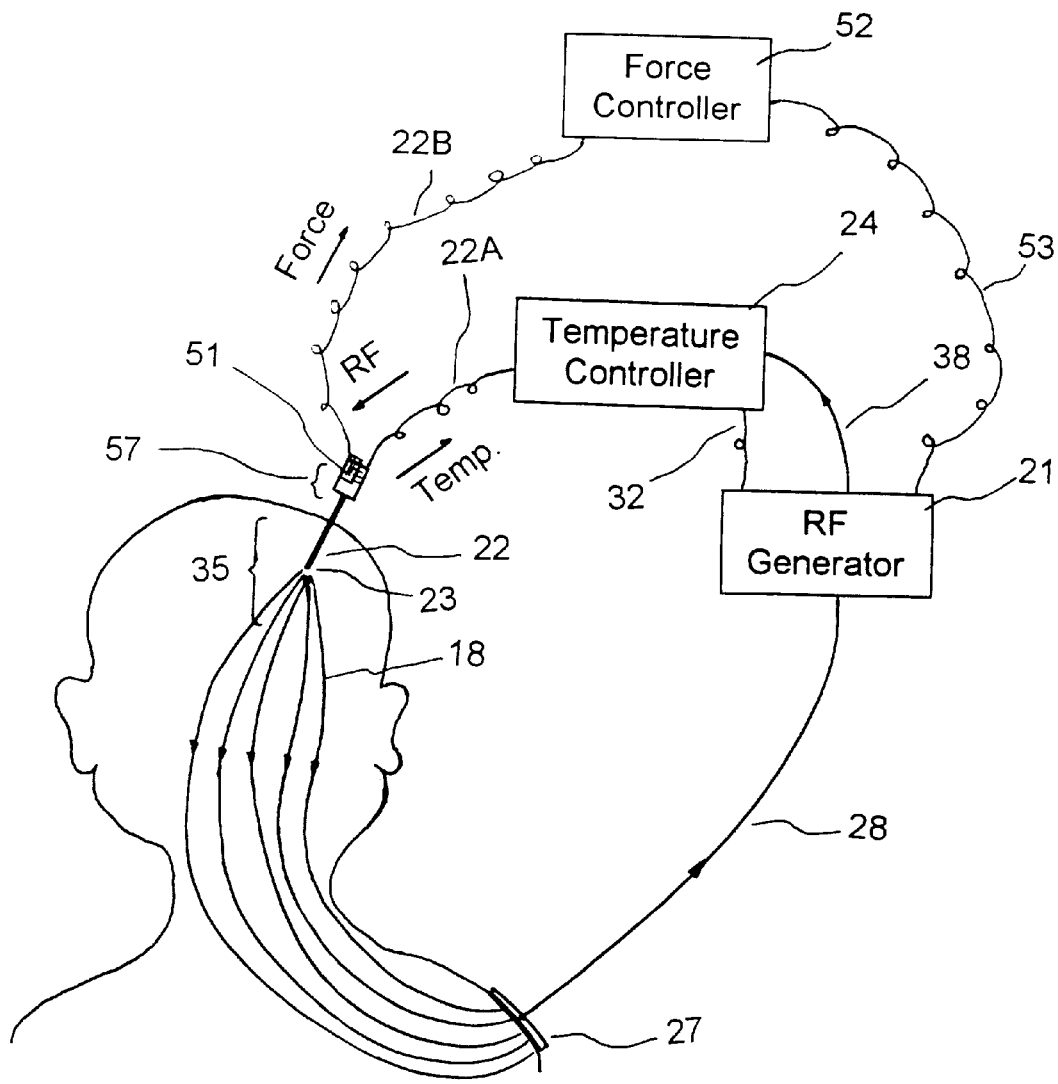
FIG. 2 is an overall view of an ablation apparatus system in relation to the RF circuit, the force monitoring route, and the temperature monitoring route, constructed in accordance to the principles of the present invention.

FIG. 2 shows an overall view of an ablation apparatus system in relation to the RF circuit, the force monitoring route, and the temperature monitoring route, constructed in accordance to the principles of the present invention. As illustrated and shown in FIG. 2, a temperature sensing probe 23 functioning also as an ablation apparatus is inserted into a brain portion 35 of a patient for tissue treatment. The RF voltage for the generator 21 causes current to flow through the temperature sensing wire 22A, 22 through the temperature sensing probe 23, and through the patient's body 35, which is a conductive electrolytic medium. Thus, patient's body becomes part of the RF circuit. The current 18 spreads out from the temperature sensing probe 23 and flows through the electrolytic tissue medium of the body. In the meantime, the temperature sensing wire 22, 22A transmits temperature reading from the temperature sensing probe 23 to a temperature controller 24 and relayed the controlling signal through a connecting medium 32 to the RF generator 21.

The force exerted by a contact tissue to the temperature sensing probe 23 is transmitted through a rigid portion of the temperature sensing wires 22 to a force sensing means 51 on a proximal portion 57 of the ablation apparatus. Therefrom, the force sensed is relayed through the force transmission wire 22B to a force controller 52. In one further embodiment, the force signal is relayed through a medium 53 to the RF generator 21 for controlling the RF delivery.

Figure 3:
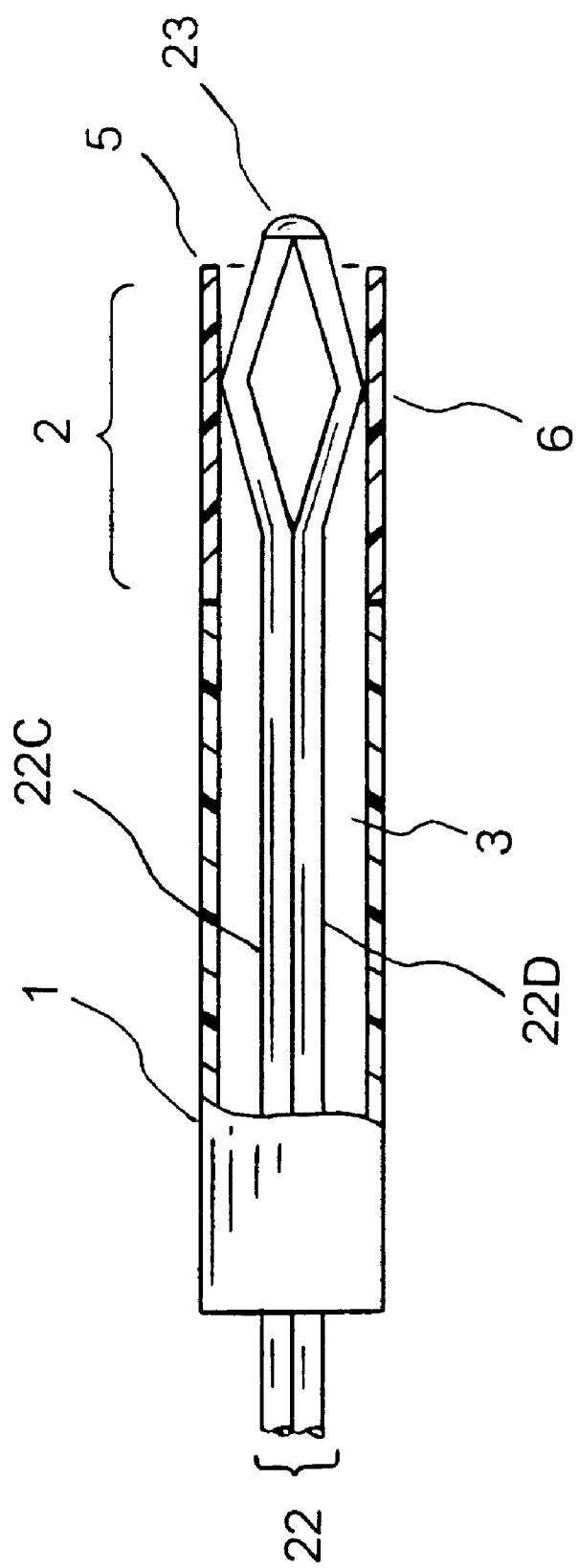
FIG. 3 is a cross-sectional view of a distal end portion of a preferred apparatus having a thermocouple sensing probe as a RF delivery electrode.

FIG. 3 shows a cross-sectional view of a distal end portion of the apparatus having a thermocouple sensing probe 23 as temperature sensing means and RF delivery electrode means. In a preferred embodiment, the temperature sensing probe 23 is enclosed within an elongate tubular shaft 1 for protection and/or strength supporting, having a shaft proximal end, a shaft distal end 5, and a shaft lumen 3. A distal portion 2 of the elongate tubular shaft 1 may be made of conductive material and is in contact with the temperature sensing probe 23 or the temperature sensing wire 22C, 22D at a contact point 6, wherein the sensing probe 23 is secured to an external RF generator through a temperature sensing wire 22. In one alternate embodiment, at least one temperature sensing wire 22C, 22D is rigid and adopted for transmitting the force sensed at the tip 23 to the force sensing means 51.

Figure 4:
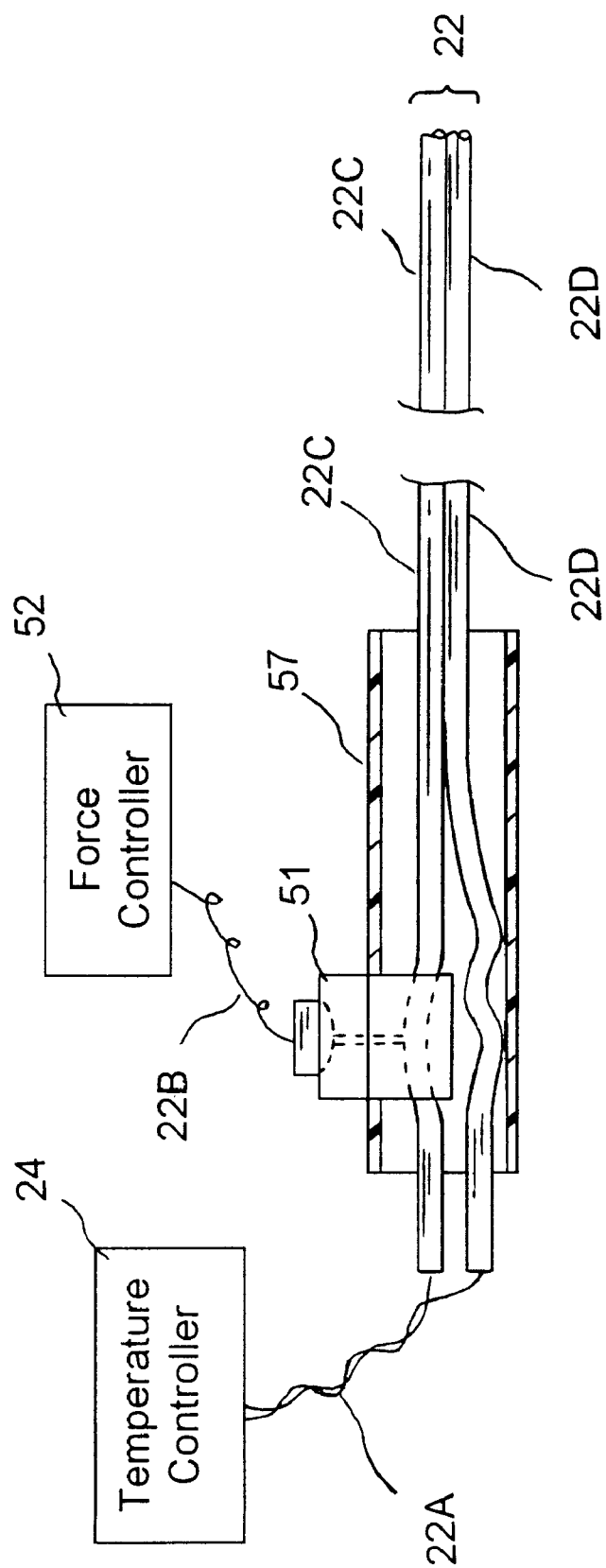
FIG. 4 is a cross-sectional view of a proximal end portion of the preferred apparatus having force measuring means including a force measuring mechanism and a force controller.

FIG. 4 shows a cross-sectional view of a proximal end portion 57 of the preferred apparatus having force measuring means including a force measuring mechanism 51 and a force controller 52. The force sensed at the tip 23 is transmitted through an wire 22C to a force measuring mechanism 51, wherein the other wire 22D is relaxed and does not exert any force to the force measuring mechanism 51. The force measuring mechanism may be selected from a group consisting of a strain gauge, a spring instrument, a cantilever instrument, a piezoelectric transducer, piezoresistive transducer, an elastic-element measuring device and the like. The temperature sensed from the tip 23 is also transmitted through sensing wires 22C, 22D and 22A to a temperature controller 24.

To keep the electrode means at its minimal dimension, a spherical or needle-like probe may be constructed for the thermocouple probe 23 as shown in FIG. 3. The temperature sensing wire 22, 22A, 22B, 22C, 22D is usually coated by an insulating material.

The RF energy delivery is controlled by using the measured temperature from the temperature sensing probe 23, through a closed-loop temperature control mechanism 24 and/or algorithm. The RF energy delivery may also be controlled by using the measured force from the force measuring probe 23 of the force measuring means 51, through a closed-loop force control mechanism 52 and/or algorithm. When the measured temperature or force rises to the preset high-limit point, the control mechanism sends out a signal to cut off the RF energy supply. In a similar manner, when the measured temperature or force drops to the preset low-limit point, the control mechanism sends out a signal to activate the RF energy supply.

During operations, the method comprises steps of (a) inserting said ablation apparatus of the present invention through an opening to a location of the tissue to be treated; (b) positioning the temperature sensing probe at the tissue to be treated; and (c) applying RF current through the at least one temperature sensing wire to the temperature sensing probe to effect treatment of the tissue.

The external RF energy generator means has the capability to supply RF energy by controlling the mode, time, power, and temperature through an optional separate closedloop control means. The patient is connected to the RF generator means through a DIP electrode to form a closed-loop current system. Therefore, RF energy is applied and delivered to the targeted tissue through the electrode means of this invention, wherein the electrode means may comprise a temperature sensing probe electrode or a regular electrode. The radiofrequency energy current in this invention is preferably within the range of 50 to 2,000 kHz. In a particular embodiment, the material for the electrode means of this invention consists of conductive metals such as platinum, iridium, gold, silver, copper, Constantan, stainless steel, Nitinol, or an alloy of these metals.

From the foregoing description, it should now be appreciated that an ablation apparatus system for the treatment of tissues in a difficult-to-access location comprising a RF energy source through the sensing wire and temperature sensing probe for temperature sensing means and force measuring means has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation apparatus comprising:

temperature sensing means for measuring temperature, wherein said temperature sensing means comprises a temperature sensing probe and at least one temperature sensing wire secured to the temperature sensing probe, the temperature sensing probe being adapted for tissue contact, wherein a source of RF current connects to one of the at least one temperature sensing wire of the temperature sensing means, and being adapted for delivering RF current to the temperature sensing probe; and force measuring means for measuring force exerted onto the temperature sensing probe by contacted tissue.

2. The ablation apparatus of claim 1, wherein one of the at least one temperature sensing wire is a rigid wire for transmitting force for the force measuring means.

3. The ablation apparatus as in claim 1 further comprising temperature control means for receiving temperature reading, wherein temperature measured from the temperature sensing means is relayed to the temperature control means and is adapted to effect RF current delivery to the temperature sensing probe of the ablation apparatus.

4. The ablation apparatus as in claim 2 further comprising force control means for receiving force reading, wherein force reading measured from the force measuring means is relayed to the force control means and is adapted to effect RF current delivery to the temperature sensing probe of the ablation apparatus.

5. The ablation apparatus of claim 1, wherein RE current is within the range of 50 to 2,000 kHz.

6. The ablation apparatus of claim 1, wherein the temperature sensing probe is selected from a group consisting of a thermocouple type temperature probe, a thermistor type temperature probe, and a bimetal thermometer type temperature probe.

7. The ablation apparatus of claim 1, wherein the force measuring means is selected from a group consisting of a strain gauge, a spring instrument, a cantilever instrument, a piezoelectric transducer, piezoresistive transducer, and an elastic-element measuring device.

8. The ablation apparatus of claim 1, wherein the temperature sensing means and force measuring means are enclosed within an elongate tubular shaft for protection.

9. The ablation apparatus of claim 8, wherein the elongate tubular shaft further comprises a fluid passageway adapted for receiving fluid from a fluid source and venting fluid out of the elongate tubular shaft.

10. The ablation apparatus of claim 8, wherein a distal portion of the elongate tubular shaft is conductive and is in contact with a portion of the temperature sensing means.

11. A method for treating a tissue of a patient, the method comprising the steps of:

(a) inserting an ablation apparatus through an opening to a location of the tissue to be treated, the ablation apparatus comprising temperature sensing means for measuring temperature, wherein said temperature sensing means comprises a temperature sensing probe and at least one temperature sensing wire secured to the temperature sensing probe, the temperature sensing probe being adapted for tissue contact, wherein a source of RF current connects to one of the at least one temperature sensing wire of the temperature sensing means, and being adapted for delivering RF current to the temperature sensing probe; and force measuring means for measuring force exerted onto the temperature sensing probe by contacted tissue;

(b) positioning the temperature sensing probe at the tissue to be treated; and (c) applying RF current through one of the at least one temperature sensing wire to the temperature sensing probe to effect treatment of the tissue.

12. The method for treating a tissue of a patient as in claim 11, the ablation apparatus further comprising temperature control means for receiving temperature readings, the method further comprising relaying measured temperature from the temperature sensing probe to the temperature control means, adapted to effect the RF current delivery to the temperature sensing probe of the ablation apparatus.

13. The method for treating a tissue of a patient as in claim 12, wherein the tissue is selected from a group consisting of a liver tissue, a tumor, a cancer, a prostate, a canker, a capillary, a brain tissue, and a nerve tissue.

14. The method for treating a tissue of a patient as in claim 11, the ablation apparatus further comprising force control means for receiving force readings, the method further comprising relaying measured force to the force control means, adapted to effect the RF current delivery to the temperature sensing probe of the ablation apparatus.

* * * * *